US009409837B2

(12) United States Patent
Brummer et al.

(10) Patent No.: US 9,409,837 B2
(45) Date of Patent: Aug. 9, 2016

(54) BUTADIENE EXTRACTION PROCESS

(71) Applicant: Lummus Technology Inc., Bloomfield, NJ (US)

(72) Inventors: Robert John Brummer, Wharton, NJ (US); Kevin John Schwint, Long Valley, NJ (US); Thomas Alexander Dwyer, Bloomfield, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 159 days.

(21) Appl. No.: 14/034,822

(22) Filed: Sep. 24, 2013

(65) Prior Publication Data

US 2014/0100399 A1   Apr. 10, 2014

Related U.S. Application Data

(60) Provisional application No. 61/709,581, filed on Oct. 4, 2012.

(51) Int. Cl.
*C07C 5/09* (2006.01)
*C07C 7/167* (2006.01)
*C07C 7/00* (2006.01)

(52) U.S. Cl.
CPC . *C07C 5/09* (2013.01); *C07C 7/005* (2013.01); *C07C 7/167* (2013.01)

(58) Field of Classification Search
None
See application file for complete search history.

(56) References Cited

U.S. PATENT DOCUMENTS

| 3,293,316 | A | 12/1966 | Weitz et al. |
| 4,049,742 | A | 9/1977 | Weitz et al. |
| 4,277,313 | A | 7/1981 | Mehra et al. |
| 4,310,388 | A | 1/1982 | Volkamer et al. |
| 7,132,038 | B2 | 11/2006 | Bohner et al. |
| 7,226,527 | B2 | 6/2007 | Bohner et al. |
| 7,393,992 | B2 | 7/2008 | Hill et al. |
| 7,482,500 | B2 | 1/2009 | Johann et al. |
| 2003/0181772 | A1 | 9/2003 | Meyer et al. |

FOREIGN PATENT DOCUMENTS

| CN | 1590353 A | 3/2005 |
| CN | 1590513 A | 3/2005 |
| GB | 1428228 A | 3/1976 |
| WO | 2010008109 A1 | 1/2010 |

OTHER PUBLICATIONS

International Search Report and Written Opinion mailed Jan. 23, 2014 in corresponding International Application No. PCT/US2013/060515 (10 pages).
First Office Action issued Feb. 14, 2016 in corresponding Chinese application No. 201380056150.8 (w/translation) (17 pages).
Extended European Search Report issued in European Application No. 13843770.2; Dated Jun. 2, 2016 (9 pages).

*Primary Examiner* — Tam M Nguyen
(74) *Attorney, Agent, or Firm* — Osha Liang LLP

(57) ABSTRACT

A process for recovering butadiene from a $C_4$ fraction is disclosed. The process may include: contacting a mixed $C_4$ stream comprising butane, butene, and butadiene, with a solvent comprising an organic solvent and water in a butadiene pre-absorber column to recover an overheads fraction comprising at least a portion of the butane, butene, and water, and a first bottoms fraction comprising the organic solvent, butadiene, and at least a portion of the butene; and feeding the first bottoms fraction to a butadiene extraction unit to recover a butene fraction, a crude butadiene fraction, and a solvent fraction.

16 Claims, 4 Drawing Sheets

BUTADIENE EXTRACTION PROCESS

CROSS-REFERENCE TO RELATED APPLICATIONS

This application, pursuant to 35 U.S.C. §119(e), claims priority to U.S. Provisional Application Ser. No. 61/709,581, filed Oct. 4, 2012, which is herein incorporated by reference in its entirety.

FIELD OF THE DISCLOSURE

Embodiments disclosed here relate to recovery of butadiene from a mixed hydrocarbon stream. More specifically, embodiments disclosed herein relate to the recovery of butadiene from a mixed $C_4$ hydrocarbon stream, integrating post-extraction selective hydrogenation with butadiene extraction unit feed preparation to improve the efficiency and cost effectiveness of processes for the recovery of butadiene.

BACKGROUND

Butadiene is an important base chemical and is used, for example, to prepare synthetic rubbers (butadiene homopolymers, styrene-butadiene-rubber or nitrile rubber) or for preparing thermoplastic terpolymers (acrylonitrile-butadiene-styrene copolymers). Butadiene is also converted to sulfolane, chloroprene and 1,4-hexamethylenediamine (via 1,4-dichlorobutene and adiponitrile). Dimerization of butadiene also allows vinylcyclohexene to be generated, which can be dehydrogenated to form styrene.

Butadiene can be prepared from saturated hydrocarbons by refining process or by thermal cracking (steam cracking) processes, in which case naphtha is typically used as the raw material. In the course of refining or steam cracking of naphtha, a mixture of methane, ethane, ethene, acetylene, propane, propene, propyne, allene, butenes, butadiene, butynes, methylallene, $C_4$ and higher hydrocarbons are obtained.

Typical processes to recover butadiene from mixed $C_4$ streams include extractive distillation processes, which may incorporate use of selective solvents. Examples of extractive distillation processes are found, for example, in U.S. Pat. Nos. 7,393,992, 7,482,500, 7,226,527, 4,310,388, and 7,132,038, among others.

The butadiene recovery processes typically use 3- or 4-column extractive distillation systems to separate a mixed $C_4$ stream into product fractions, including a lights/butane/butenes stream (Raffinate-1 product), a crude butadiene product, which may be sent to a conventional distillation system for further purification, and $C_3$ acetylenes (propyne) and $C_4$ acetylenes streams, which may be sent to a selective hydrogenation unit, for example.

The $C_3$ and $C_4$ acetylenes may be selectively hydrogenated downstream of the butadiene recovery process to form useful olefins and dienes. Formation of olefin oligomers (green oil) may result during such hydrogenation processes. Processing of the crude $C_4$'s at elevated temperatures through extractive and conventional distillation may also result in formation of dimers and oligomers, such as vinyl cyclohexane. In other processes for the recovery of butadiene, the totality of a crude $C_4$ stream may be passed through a selective hydrogenation reactor to selectively hydrogenate acetylenes upstream of extractive distillation. Following such hydrogenation systems, it is typical to separate the oligomeric "green oil" byproducts from the desired hydrocarbon products using a separator commonly referred to as a green oil column.

In addition to the acetylene streams, 1,2-butadiene and $C_{5+}$ components are also recovered from the butadiene separation processes. Other waste streams may also be produced during the various butadiene recovery processes. For example, butadiene vaporization may require the removal of non-vaporized components from a vaporizer drum.

SUMMARY

Embodiments disclosed herein provide improved processes for recovering butadiene from mixed $C_4$ hydrocarbon streams. More specifically, embodiments disclosed herein provide for the recovery of butadiene from a mixed $C_4$ hydrocarbon stream, integrating post-extraction selective hydrogenation with butadiene extraction unit feed preparation to improve the efficiency and cost effectiveness of processes for the recovery of butadiene. Such integration may provide one or more of the following advantages including decreased 1,2-butadiene rejection, a reduction in the number of waste streams, a reduction in the overall energy requirements, and/or a reduction in the total number of vessels or unit operations required to perform the separations, each of which may improve the efficiency and cost effectiveness of processes for the recovery of butadiene.

In one aspect, embodiments disclosed herein relate to a process for recovering butadiene from a $C_4$ fraction. The process may include: feeding a hydrocarbon fraction containing butanes, butenes, 1,2-butadiene, 1,3-butadiene, $C_4$ acetylenes, $C_3$ acetylenes, and $C_{5+}$ hydrocarbons to a butadiene extraction unit; recovering from the butadiene extraction unit a 1,3-butadiene fraction, a $C_3$ acetylene fraction, a $C_4$ acetylene fraction, one or more fractions comprising the butanes and butenes, and a fraction comprising the 1,2-butadiene and the $C_{5+}$ hydrocarbons; selectively hydrogenating at least one of the $C_3$ acetylene fraction and the $C_4$ acetylene fraction to produce a hydrogenated effluent comprising olefins, dienes, and oligomer byproducts; feeding the hydrogenated effluent and the fraction comprising the 1,2-butadiene and the $C_{5+}$ hydrocarbons to a separator to recover a heavies fraction comprising the $C_{5+}$ hydrocarbons and the oligomer byproducts and a lights fraction comprising the olefins, dienes, and 1,2-butadiene; and feeding the lights fraction to the butadiene extraction unit.

In another aspect, embodiments disclosed herein relate to a process for recovering butadiene from a $C_4$ fraction. The process may include: feeding a hydrocarbon fraction containing butanes, butenes, 1,2-butadiene, 1,3-butadiene, $C_4$ acetylenes, $C_3$ acetylenes, and $C_{5+}$ hydrocarbons to a vaporization system; recovering a vapor fraction from the vaporization system; recovering a liquid fraction from the vaporization system; feeding the recovered vapor fraction to a butadiene extraction unit; recovering from the butadiene extraction unit a 1,3-butadiene fraction, a $C_3$ acetylene fraction, a $C_4$ acetylene fraction, one or more fractions comprising the butanes and butenes, and a fraction comprising the 1,2-butadiene and the $C_{5+}$ hydrocarbons; selectively hydrogenating at least one of the $C_3$ acetylene fraction and the $C_4$ acetylene fraction to produce a hydrogenated effluent comprising olefins, dienes, and oligomer byproducts; feeding the hydrogenated effluent and the fraction comprising the 1,2-butadiene and the $C_{5+}$ hydrocarbons to a separator to recover a heavies fraction comprising the $C_{5+}$ hydrocarbons and the oligomer byproducts and a lights fraction comprising the olefins, dienes, and 1,2-butadiene; feeding the recovered liquid fraction to the separator as a reflux; and feeding the lights fraction to the butadiene extraction unit.

Other aspects and advantages of the invention will be apparent from the following description and the appended claims.

DETAILED DESCRIPTION

Figure 1:
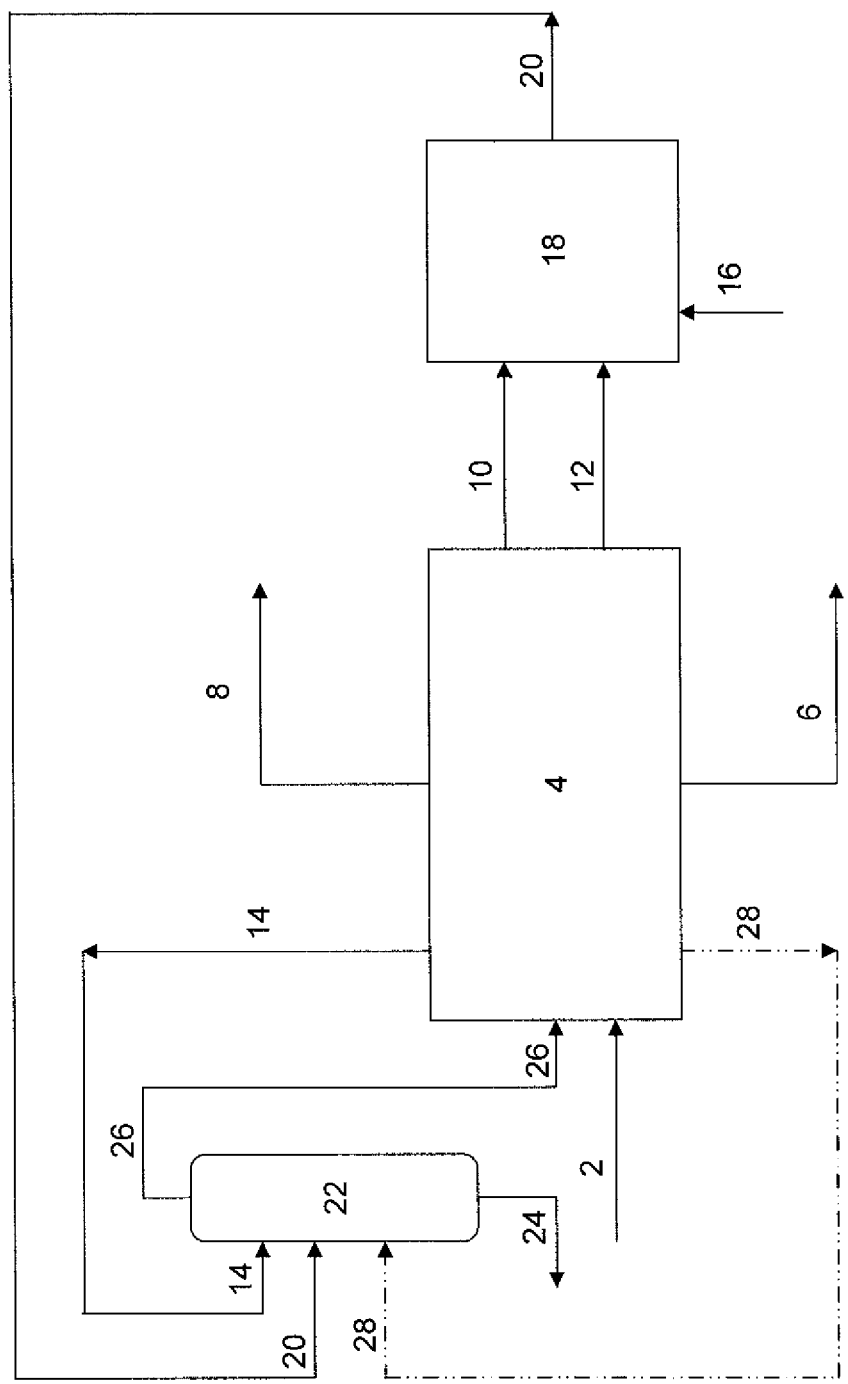
FIG. 1 is a simplified flow diagram of a process for butadiene recovery according to embodiments disclosed herein.

Embodiments disclosed here relate to recovering butadiene from mixed $C_4$ hydrocarbon streams. More specifically, embodiments disclosed herein relate to improving the operations of butadiene extraction processes coupled to one or more downstream selective hydrogenation units.

The $C_4$ fraction to be used as starting mixture in the present processes is a mixture of hydrocarbons having predominantly four carbon atoms per molecule. $C_4$ fractions are obtained, for example, in the preparation of ethylene and/or propylene by thermal or catalytic cracking of a petroleum fraction, such as liquefied petroleum gas, light naphtha or gas oil. $C_4$ fractions may also be obtained by the catalytic dehydrogenation (oxidative and/or non-oxidative dehydrogenation) of n-butane and/or n-butene. The resulting $C_4$ fractions generally include butanes, n-butene, isobutene, 1,3-butadiene and small amounts of $C_3$ and $C_5$ hydrocarbons, including methylacetylene, as well as butynes, in particular 1-butyne (ethylacetylene) and butenyne (vinylacetylene). The 1,3-butadiene content is generally from 5 to 80% by weight. For example, a cracker or a CATADIENE unit may contain 15 to 17% butadiene, by weight. Other mixed $C_4$ feed streams may contain greater or lesser amounts of butadiene. When present in the mixed feed stream, vinylacetylene may be selectively hydrogenated to the desired 1,3-butadiene product prior to feed of the mixed $C_4$ stream to the butadiene extraction unit. In some embodiments, the mixed $C_4$ hydrocarbon stream may be provided, for example, by at least one of cracking, oxidatively dehydrogenating, and non-oxidatively dehydrogenating a $C_4$ hydrocarbon stream comprising butane in one or more dehydrogenation reactors to produce a product gas stream comprising butane, butene, and butadiene.

The above-described hydrocarbon fraction, containing butanes, butenes, 1,2-butadiene, 1,3-butadiene, $C_4$ acetylenes, $C_3$ acetylenes, and $C_{5+}$ hydrocarbons, is fed to a butadiene extraction unit for separation and recovery of the various hydrocarbons, including one or more lights/butanes/butenes fractions (commonly referred to as a Raffinate-1 product), a 1,3-butadiene fraction, a $C_3$ acetylenes (propyne) fraction, a $C_4$ acetylenes fraction, which may include a portion of the 1,2-butadiene, and a heavies fraction, which may include a portion of the 1,2-butadiene and the $C_{5+}$ hydrocarbons. In some embodiments, dimers of butadiene may be formed upstream of the butadiene extraction unit or during processing of the hydrocarbon fraction within the butadiene extraction unit. The vinylcyclohexene components may be recovered with the heavies fraction, or may be recovered as a separate fraction containing vinylcyclohexene.

1,2-Butadiene may thus be recovered in two fractions, the heavies fraction and the $C_4$ acetylenes fraction. For example, 20-80% of the feed 1,2-butadiene may be recovered in the heavies fraction, and 80-20% of the feed 1,2-butadiene may be recovered in the $C_4$ acetylenes fraction, depending upon the conditions in the butadiene extraction unit and the solvent used, among other factors.

The $C_4$ acetylenes fraction and/or the $C_3$ acetylenes fraction may be fed to a downstream hydrogenation reactor or further processed to produce desired end products. Hydrogenation of the $C_3$ acetylene fraction and/or the $C_4$ acetylene fraction may be used to produce olefins, such as propylene and/or butenes. Over-hydrogenation may result in the production of alkanes, and byproducts of the hydrogenation process may include oligomeric byproducts (the aforementioned "green oil"). The oligomeric byproducts are then removed from the hydrogenated effluent in a separator, such as a green oil column, and the olefinic and paraffinic hydrogenation products may be recovered.

In prior processes, the heavies fraction recovered in the butadiene extraction unit is typically sent to fuel or recycled to a cracker or other upstream processes. The heavies fraction may also include minor amounts of solvent, such as N-methylpyrrolidone (NMP) or polymerization inhibitors, such as tertiary butyl catechol, which may both act as a hydrogenation catalyst poison. Thus, it was heretofore undesirable to feed the heavies fraction, including the 1,2-butadiene, to a downstream hydrogenation unit for conversion of the 1,2-butadiene to valuable end products, such as butenes, due to the required pretreatment expense to remove the undesired impurities.

It has been found, however, that co-processing of the heavies fraction and the hydrogenation reactor effluent in the separator (green oil column) may provide for an efficient means reduce the number of waste streams. The heavies fraction and the effluent from the hydrogenation reactor may be fed to the separator, where the oligomeric byproducts and the $C_{5+}$ hydrocarbons may be recovered as a bottoms fraction, and the 1,2-butadiene may be recovered as an overheads along with the olefinic and paraffinic hydrogenation products. The overheads may then be recycled back to the butadiene extraction unit for recovery of the olefinic and paraffinic hydrogenation products with their respective fractions (Raffinate-1, for example).

Operation of the system in this manner may recycle 1,2-butadiene through the butadiene extraction unit, allowing the 1,2-butadiene concentration to build up such that the 1,2-butadiene in the hydrocarbon feed to the butadiene extraction unit exits via the $C_4$ acetylene fraction. In other words, the 1,2-butadiene mass balance for the overall system is maintained as the amount of 1,2-butadiene in the $C_4$ acetylene fraction is approximately equal to an amount of the 1,2-butadiene in the feed hydrocarbon fraction.

In some embodiments, as noted above, the $C_4$ acetylene fraction may used as the feed or a feed component to the hydrogenation reactor for conversion of the $C_4$ acetylenes to valuable $C_4$ dienes and olefins. Operation of the system in this manner may also recycle 1,2-butadiene in the heavies through the butadiene extraction unit, allowing the 1,2-butadiene concentration to build up such that the 1,2-butadiene in the hydrocarbon feed to the butadiene extraction unit exits via the $C_4$ acetylene fraction and is subsequently hydrogenated. In other words, the 1,2-butadiene mass balance for the overall system is maintained as the amount of 1,2-butadiene hydrogenated in the selective hydrogenation reactor may be approximately equal to an amount of the 1,2-butadiene in the feed hydrocarbon fraction. When the heavies fraction and $C_4$ acetylenes are processed in this manner, the number of waste streams may be reduced, the volume of waste may be reduced (the hydrogenated 1,2-butadiene), and valuable end products may be produced and recovered (again, the hydrogenated 1,2-butadiene). Routing the streams in this manner also effectively allows the undesired impurities to exit with the bottoms fraction recovered from the green oil separator, thus minimizing or avoiding contact of these impurities with the hydrogenation catalyst.

The green oil column may also be used to realize efficiencies with respect to feed vaporization in some embodiments. As noted above, the overhead of the green oil column may be sent to the butadiene extraction unit. The $C_4$ hydrocarbon feed is typically fed to the butadiene extraction unit as a vapor, and must be vaporized prior to being fed to the butadiene extraction unit. A portion of the mixed $C_4$ hydrocarbon feed may be fed to the green oil column as reflux. In this manner, the need for a condenser and reflux system for the green oil column may be eliminated, completely eliminating the cooling requirements for the green oil column overheads. In addition, the heat input to the green oil column reduces the energy required in the vaporization system for vaporization of the portion of the mixed $C_4$ hydrocarbon feed that is used as reflux.

Vaporization of the $C_4$ hydrocarbon feed may be performed using one or more heat exchangers (vaporizers) and one or more vaporization drums in some embodiments, for example. Oligomers formed during the vaporization process and/or heavies in the mixed hydrocarbon feed may accumulate as a liquid in the vaporization drums. Some desirable $C_4$'s may also accumulate in the liquid phase. In some embodiments, the liquid from the vaporization drums may be used as the reflux stream fed to the green oil column. In this manner, what is typically a blowdown waste stream may be used as a process stream, allowing for the energy efficiencies noted above as well as the recovery of valuable $C_4$ components that may otherwise be lost to the vaporization waste blowdown stream. Use of the vaporization drum liquid as reflux also provides for consolidation of heavy components, recovered as a single waste stream in the green oil column bottoms.

As noted above, vinylcyclohexene components may be recovered with the heavies fraction, or may be recovered as a separate fraction containing vinylcyclohexene. Where the vinylcyclohexene components are recovered with the heavies fraction, feed of the heavies fraction to the green oil column allows the vinylcylcohexene to also be recovered in the green oil column bottoms. Where the vinylcyclohexene is recovered as a separate fraction containing vinylcyclohexene in the butadiene extraction unit, this fraction may also be fed to the green oil column so as to combine the heavy components for recovery in a single waste stream.

Referring now to FIG. 1, a simplified process flow diagram for recovering butadiene according to embodiments disclosed herein is illustrated. A mixed hydrocarbon feed including 1,2-butadiene, 1,3-butadiene, butanes, butenes, methyl acetylene, vinyl acetylene, and $C_5$ hydrocabons is fed via flow line 2 to a butadiene extraction unit 4, which may include, for example, a feed vaporizer, a main washer, a rectifier, an after-washer, and conventional distillation columns, among other unit operations (not illustrated). In the butadiene extraction unit 4, the feed components are separated into various product streams, including a 1,3-butadiene fraction 6, a Raffinate 1 (butanes and butenes) fraction 8, a methyl acetylene fraction 10, a vinyl acetylene fraction 12, and a heavies fraction 14 including 1,2-butadiene and $C_{5+}$ hydrocarbons. Vinyl acetylene fraction 12 may include both vinyl acetylene and 1,2-butadiene.

One or both of the vinyl acetylene and methyl acetylene streams 10, 12 may then contacted with hydrogen, fed via flow line 16, over a selective hydrogenation catalyst in a hydrogenation reactor 18 for conversion of the acetylenes contained in the respective streams to dienes, olefins, and paraffins, which may be recovered as an effluent via flow line 20.

In addition to the desired hydrogenation products, oligomers may be produced and recovered in effluent 20. To separate the desired hydrogenation products from the oligomers, the effluent 20 is fed to a green oil column 22 along with heavies fraction 14, where the oligomers and $C_{5+}$ components are recovered as a bottoms fraction 24 and the dienes, olefins, and paraffins, including the 1,2-butadiene contained in the heavies fraction, are recovered as an overheads fraction 26. Although not illustrated, separations in green oil column 22 may be facilitated by use of a reboiler and an overhead condensation system. In some embodiments, a vinylcyclohexene fraction 28 may be recovered from butadiene extraction unit 4 and forwarded to green oil column 22. Bottoms fraction 24 is thus a consolidated waste stream including heavies and oligomers.

The desired hydrogenation products (dienes, olefins, and/or paraffins) in effluent 20 and the 1,2-butadiene in fraction 14 are recovered in overheads fraction 26, which is then fed to butadiene extraction unit 4 for separation of the hydrogenation products along with mixed hydrocarbon feed 2. The 1,2-butadiene recirculates through the system in this manner. 1,2-Butadiene may also exit butadiene extraction unit 4 via vinyl acetylene fraction 12. Recirculation of butadiene via flow lines 14 and 26 may result in some accumulation of butadiene within the system. However, consumption of 1,2-butadiene in hydrogenation reactor 18 provides for an outlet for the 1,2-butadiene, such that the overall mass balance for 1,2-butadiene may be satisfied and an excessive accumulation of 1,2-butadiene within butadiene extraction unit 4 does not occur.

Figure 2:
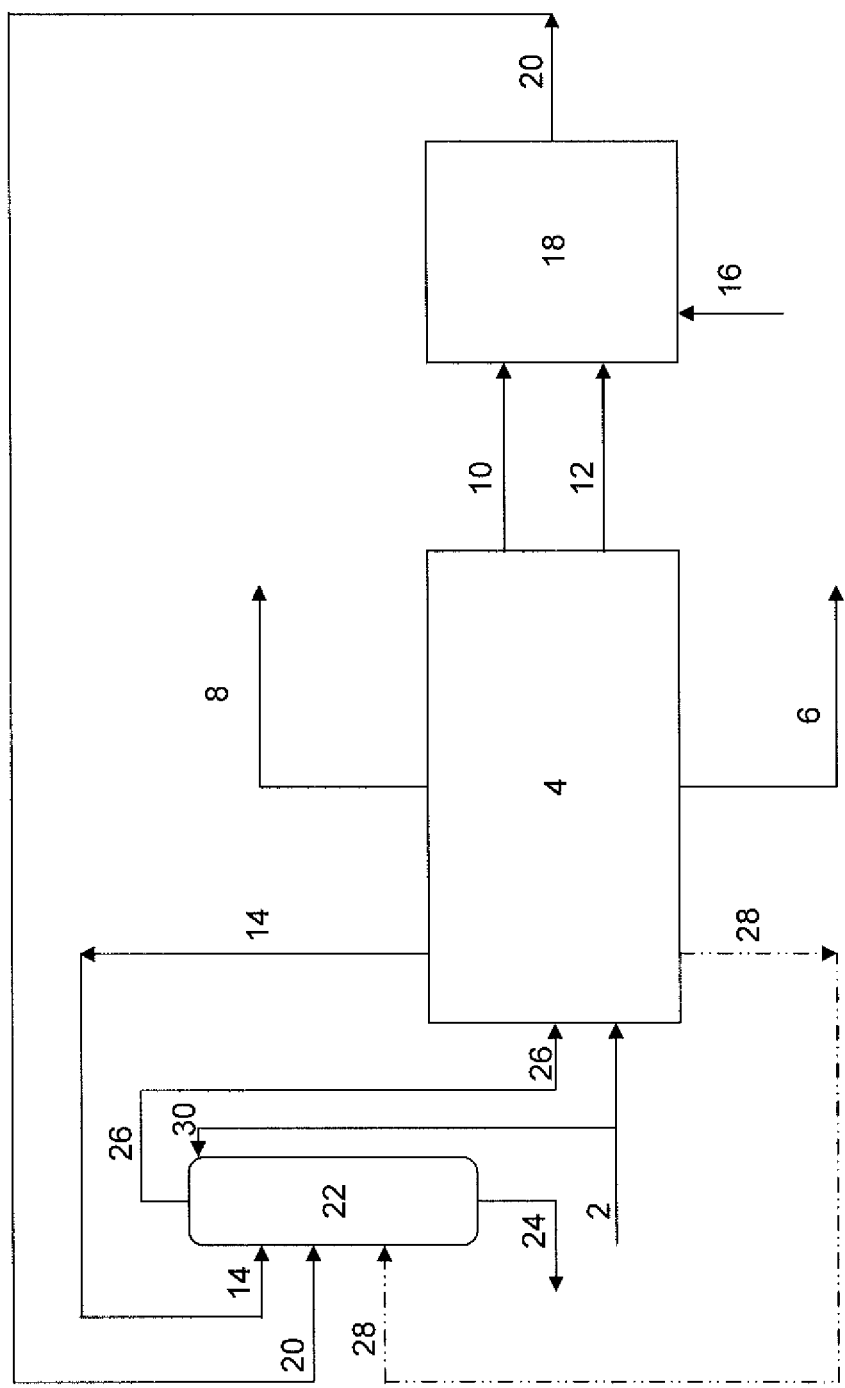
FIG. 2 is a simplified flow diagram of a process for butadiene recovery according to embodiments disclosed herein.

Referring now to FIG. 2, a simplified process flow diagram for recovering butadiene according to embodiments disclosed herein is illustrated, where like numerals represent like parts. In this embodiment, a portion 30 of mixed hydrocarbon feed 2 may be fed as a reflux to green oil column 22. The remaining portion of the mixed hydrocarbon feed may be fed to butadiene extraction unit 4 for processing as described above. The $C_4$ components in reflux portion 30 may facilitate separation of the oligomers and heavies fed via flow lines 14, 20, 28, and be vaporized and recovered in overheads fraction 26. In this manner, the overhead condensation system for green oil column 22 may be eliminated, where the vapors are sent directly to butadiene extraction unit 4 for processing, and the necessary reflux is provided via a portion of the mixed hydrocarbon feed. Capital costs and operational costs may thus be reduced. It is also noted that the decrease in heat duty requirements in the feed vaporization section of butadiene extraction unit 4 are offset by heating requirements in the green oil column 22.

Figure 3:
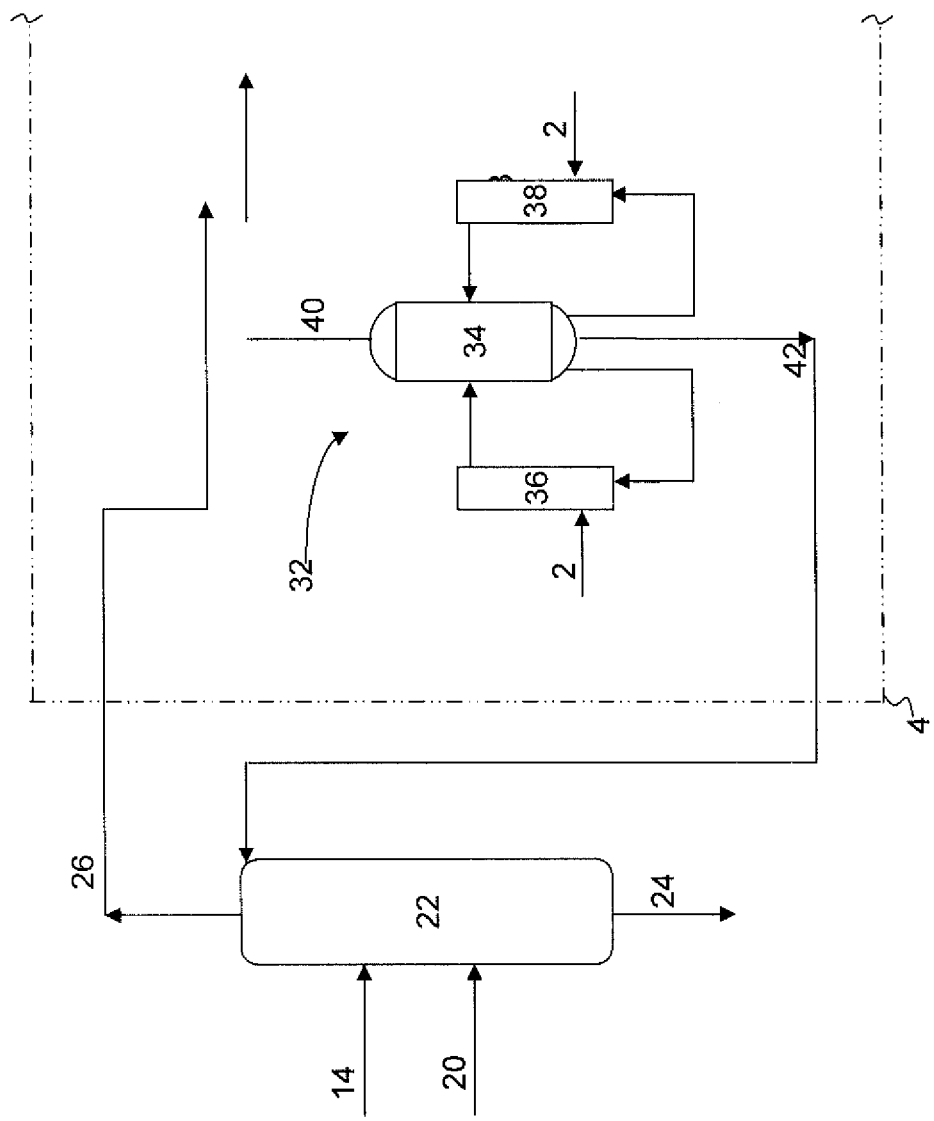
FIG. 3 is a simplified flow diagram of a process for butadiene recovery according to embodiments disclosed herein.

Referring now to FIG. 3, a simplified process flow diagram for recovering butadiene according to embodiments disclosed herein is illustrated, where like numerals represent like parts. As an alternative method for providing reflux to green oil column, the mixed hydrocarbon feed 2 may be fed to the feed vaporizer system 32 of butadiene extraction unit 4. Feed vaporization system 32 may include a vaporization drum 34 and one or more heat exchangers (feed vaporizers) 36, 38 to vaporize the mixed hydrocarbon feed. The vaporized feed is recovered via flow line 40 and fed along with overheads fraction 26 to the butadiene extraction system (the pre-absorber, pre-fractionation, main washer, or other components as appropriate for the specific processing scheme used in butadiene extraction unit 4). Heavies and other components, possibly including various $C_4$ hydrocarbons, that are not vaporized accumulate in vaporization drum 34. These accumulated components are then fed via flow line 42 as reflux to green oil column 22. In this manner, the blowdown waste stream 42 from vaporization drum 34 may beneficially be used as a reflux stream, and the heavies and oligomers in streams 42, 14, 20, 28 may be consolidated into a single waste stream, and similar to the embodiment of FIG. 2, the overhead system for green oil column 22 may be eliminated.

Figure 4:
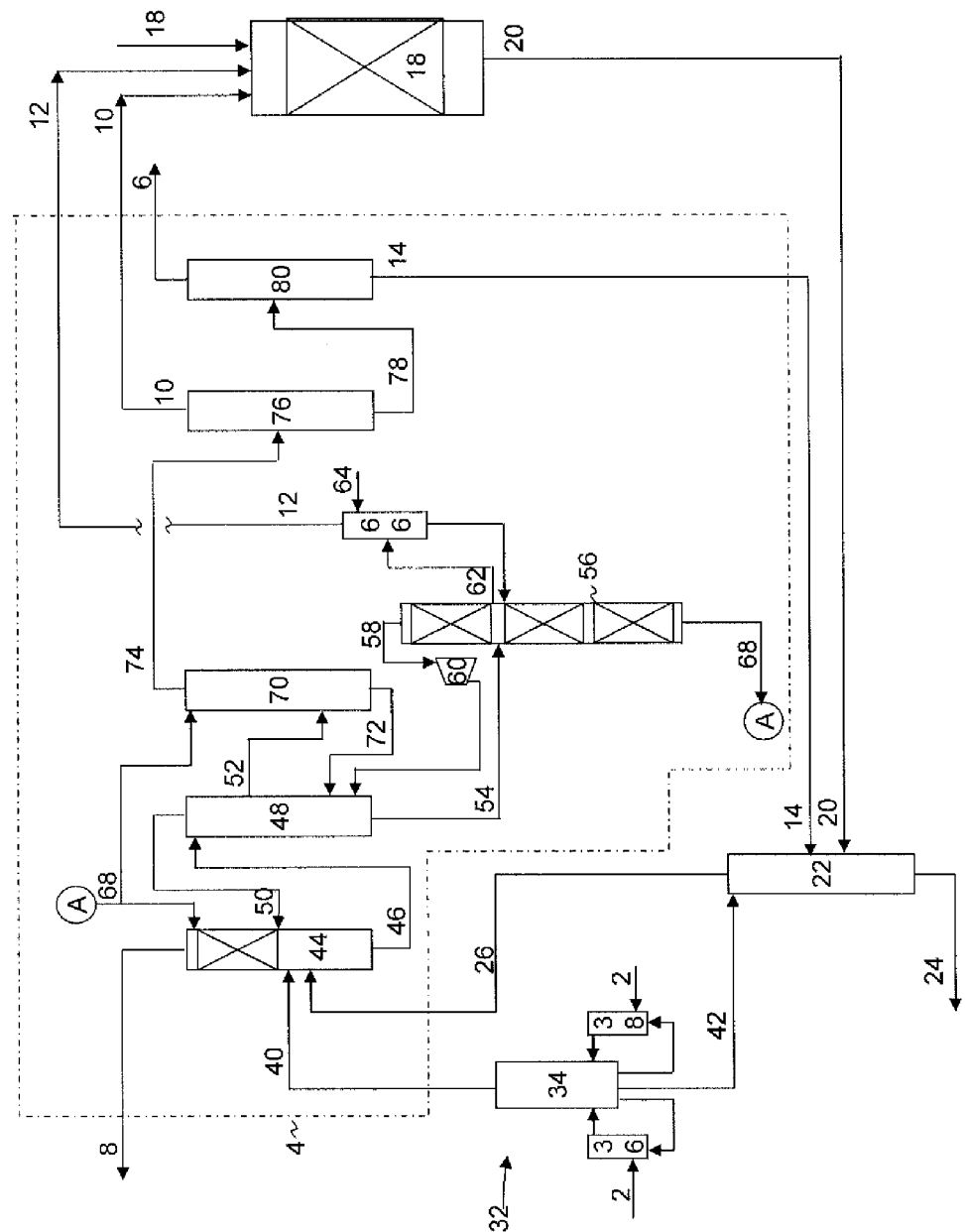
FIG. 4 is a simplified flow diagram of a process for butadiene recovery according to embodiments disclosed herein.

Referring now to FIG. 4, a simplified process flow diagram for recovering butadiene according to embodiments disclosed herein is illustrated, where like numerals represent like parts. In this embodiment, integration of post-extraction selective hydrogenation and butadiene extraction using extractive and conventional distillation is illustrated.

A mixed hydrocarbon feed 2, including butanes, butenes, 1,2-butadiene, 1,3-butadiene, methyl acetylene, vinyl acetylene, and $C_{5+}$ hydrocarbons may be fed to a feed vaporization system 32 of butadiene extraction unit 4. Feed vaporization system 32 may include a vaporization drum 34 and one or more heat exchangers (feed vaporizers) 36, 38 to vaporize the mixed hydrocarbon feed. The vaporized feed is recovered via flow line 40 and fed to main wash column 44. In main wash column 44, the vaporized feed is contacted with a solvent, such as NMP, and the butanes and butenes are separated from the more soluble 1,3-butadiene, 1,2-butadiene, methyl acetylene, vinyl acetylene, and $C_{5+}$ hydrocarbons. The butanes and butenes are recovered as an overheads fraction 8 (Raffinate 1). The enriched solvent, including the dissolved hydrocarbons, is recovered from main wash column 44 as a bottoms fraction 46.

Bottoms fraction 46 is then fed to rectifier 48 to at least partially degas the enriched solvent. Any dissolved butanes and butenes, as well as other light components may be recovered from rectifier 48 as an overheads fraction 50, which may be re-processed in main washer 44. Methyl acetylene and butadienes, including both 1,2-butadiene and 1,3-butadiene, and $C_{5+}$ hydrocarbons may be recovered from rectifier 48 as a side draw 52, and a degassed solvent, which may contain various $C_4$ components including 1,2-butadiene and vinyl acetylene, may be recovered from rectifier 48 as a bottoms fraction 54.

Bottoms fraction 54 may be fed to a degasser and cooling column(s) 56, for separation of the solvent, entrained $C_4$ components, and a vinyl acetylene fraction, which may also include 1,2-butadiene. The $C_4$ vapors may be recovered from degasser and cooling column 56 as an overheads fraction 58, which may be compressed via compressor 60 and recycled to rectifier 48. The vinyl acetylene fraction may be withdrawn from degasser and cooling column 56 as a side draw fraction 62, washed with water fed via line 64 in acetylene washer 66, and recovered as vinyl acetylene fraction 12. The degassed and cooled solvent may be recovered from degasser and cooling column 56 as a bottoms fraction 68 for recycle and feed to main wash column 44 and afterwash column 70, where the hydrocarbons in the side draw fraction 52 may be separated from the solvent. Solvent may be recovered from afterwash column 70 as a bottoms fraction 72 recycled to rectifier 48, and a crude butadiene product stream may be recovered from afterwash column 70 as an overheads fraction 74.

The crude butadiene product (overheads fraction 74) leaves the extractive distillation section and is then fed to a methyl acetylene distillation column 76, where methyl acetylene is recovered as an overheads fraction 10. The bottoms fraction 78 contains the 1,3-butadiene, 1,2-butadiene, and heavier hydrocarbons, and is fed to butadiene fractionator 80. 1,3-Butadiene having a purity of greater than 99.6% is recovered from butadiene column 80 as an overheads fraction 6, and the 1,2-butadiene and heavies are recovered as a bottoms fraction 14.

The vinyl acetylene and methyl acetylene streams 10, 12, as well as the 1,2-butadiene fraction 14, may then be processed as described with respect to FIG. 1. The vinyl acetylene and methyl acetylene streams 10, 12 are contacted with hydrogen, fed via flow line 16, over a selective hydrogenation catalyst in a hydrogenation reactor 18 for conversion of the acetylenes contained in the respective streams to dienes, olefins, and paraffins, which may be recovered as an effluent via flow line 20. Hydrogenation reactor 18 may be any type of reactor known to those skilled in the art and may contain any hydrogenation catalyst appropriate for performing the desired selective hydrogenation.

In addition to the desired hydrogenation products, oligomers may be produced and recovered in effluent 20. To separate the desired hydrogenation products from the oligomers, the effluent 20 is fed to a green oil column 22 along with heavies fraction 14, where the oligomers and $C_{5+}$ components are recovered as a bottoms fraction 24 and the dienes, olefins, and paraffins, including the 1,2-butadiene contained in the heavies fraction, are recovered as an overheads fraction 26. Although not illustrated, separations in green oil column 22 may be facilitated by use of a reboiler and an overhead condensation system. In some embodiments, a vinylcyclohexene fraction 28 may be recovered from butadiene extraction unit 4 and forwarded to green oil column 22. Bottoms fraction 24 is thus a consolidated waste stream including heavies and oligomers. The desired hydrogenation products (dienes, olefins, and/or paraffins) in effluent 20 and the 1,2-butadiene in fraction 14 are recovered in overheads fraction 26, which is then fed to butadiene extraction unit 4 for separation of the hydrogenation products along with mixed hydrocarbon feed 2.

Solvents useful in the process as illustrated in FIG. 4 may include butyrolactone, nitriles such as acetonitrile, propionitrile, methoxypropionitrile, ketones such as acetone, furfural, N-alkyl-substituted lower aliphatic amides such as dimethylformamide, diethylformamide, dimethylacetamide, diethylacetamide, N-formylmorpholine, N-alkyl-substituted cyclic amides (lactams) such as N-alkylpyrrolidones, especially N-methylpyrrolidone (NMP). In some embodiments, alkyl-substituted lower aliphatic amides or N-alkyl-substituted cyclic amides, dimethylformamide, acetonitrile, furfural or NMP are used.

In some embodiments, it is also possible to use mixtures of these extractants with one another, for example of NMP and acetonitrile, mixtures of these extractants with cosolvents and/or tert-butyl ethers, e.g. methyl tert-butyl ether, ethyl tert-butyl ether, propyl tert-butyl ether, n- or isobutyl tert-butyl ether. In other embodiments, NMP may be in aqueous solution, with from 0 to about 20 weight % water, or with from 7 to 10 weight % water, or with 8 to 8.5 weight % water in other embodiments.

Certain aspects of the processes illustrated in FIGS. 1-4 have been described with respect to butadiene recovery using an extractive and conventional distillation process, such as using aqueous NMP as a solvent (BASF type process). Embodiments disclosed herein may also provide similar benefits to other butadiene recovery processes coupled to a downstream hydrogenation reactor, such as a DMF solvent extraction process (Nippon Zeon) or an aqueous separation and acetonitrile extraction process (Shell, LyondellBassell Industries), each of which produce similar hydrocarbon fractions (Raffinate 1, acetylene(s), 1,3-butadiene, and heavies, which may include 1,2-butadiene). Thus, butadiene extraction units used in embodiments disclosed herein may include one or more of the following apparatus: a pre-absorber; a pre-fractionation column; a feed scrubber/stripper system; a main wash column; a rectifier; an afterwash column; an acetylene fractionator; a butadiene fractionator; an acetylene washer; a solvent purification system; and a degasser and cooling column; and other units as may be known to those of skill in the art.

As described above, embodiments disclosed herein provide improved processes for recovering butadiene from mixed $C_4$ hydrocarbon streams. More specifically, embodiments disclosed herein provide for the recovery of butadiene from a mixed $C_4$ hydrocarbon stream, integrating post-extraction selective hydrogenation with butadiene extraction unit feed preparation to improve the efficiency and cost effectiveness of processes for the recovery of butadiene. Such integration may advantageously provide one or more of the following advantages including decreased 1,2-butadiene rejection, a reduction in the number of waste streams, a reduction in the overall energy requirements, and/or a reduction in the total number of vessels or unit operations required to perform the separations, each of which may improve the efficiency and cost effectiveness of processes for the recovery of butadiene.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed:

1. A process for recovering 1,3-butadiene from a $C_4$ fraction, comprising:
    feeding a hydrocarbon fraction containing butanes, butenes, 1,2-butadiene, 1,3-butadiene, $C_4$ acetylenes, $C_3$ acetylenes, and $C_{5+}$ hydrocarbons to a butadiene extraction unit;
    recovering from the butadiene extraction unit a 1,3-butadiene fraction, a $C_3$ acetylene fraction, a $C_4$ acetylene fraction, one or more fractions comprising the butanes and butenes, and a fraction comprising the 1,2-butadiene and the $C_{5+}$ hydrocarbons;
    selectively hydrogenating at least one of the $C_3$ acetylene fraction and the $C_4$ acetylene fraction to produce a hydrogenated effluent comprising olefins, dienes, and oligomer byproducts;
    feeding the hydrogenated effluent and the fraction comprising the 1,2-butadiene and the $C_{5+}$ hydrocarbons to a separator to recover a heavies fraction comprising the $C_{5+}$ hydrocarbons and the oligomer byproducts and a lights fraction comprising the olefins, dienes, and 1,2-butadiene; and
    feeding the lights fraction to the butadiene extraction unit.

2. The process of claim 1, wherein the $C_4$ acetylene fraction comprises $C_4$ acetylenes and 1,2-butadiene.

3. The process of claim 2, wherein an amount of 1,2-butadiene in the $C_4$ acetylene fraction is approximately equal to an amount of the 1,2-butadiene in the feed hydrocarbon fraction.

4. The process of claim 2, wherein the $C_4$ acetylene fraction is fed to the selectively hydrogenating step, and wherein an amount of 1,2-butadiene consumed via the selectively hydrogenating is approximately equal to an amount of the 1,2-butadiene in the feed hydrocarbon fraction.

5. The process of claim 1, wherein vinylcyclohexene is produced in the butadiene extraction unit or is present in the feed hydrocarbon fraction, the process further comprising:
    recovering a fraction comprising the vinylcyclohexene from the butadiene extraction unit; and
    feeding the vinylcyclohexene fraction to the separator, wherein the vinylcyclohexene is recovered from the separator in the heavies fraction.

6. The process of claim 1, further comprising:
    feeding at least a portion of the hydrocarbon fraction to the separator as a reflux;
    vaporizing at least a portion of the hydrocarbon fraction fed to the separator;
    recovering the vaporized portion with the lights fraction for feed to the butadiene extraction unit.

7. The process of claim 6, wherein the reflux comprises only the hydrocarbon fraction or a portion thereof and wherein the lights fraction is recovered as a vapor phase fed to the butadiene extraction unit.

8. The process of claim 1, further comprising:
    vaporizing a portion of the feed hydrocarbon fraction in a vaporization system;
    recovering a vapor fraction from the vaporization system;
    recovering a liquid fraction from the vaporization system;
    feeding the recovered liquid fraction to the separator as a reflux.

9. The process of claim 8, further comprising:
    vaporizing at least a portion of the liquid fraction fed to the separator; and
    recovering the vaporized portion with the lights fraction for feed to the butadiene extraction unit.

10. The process of claim 1, wherein the fraction comprising 1,2-butadiene and $C_{5+}$ hydrocarbons further comprises at least one of N-methylpyrrolidone (NMP) and tertiary butyl catechol (TBC).

11. The process of claim 1, wherein the butadiene extraction unit comprises one or more of the following:
    a pre-absorber;
    a pre-fractionation column;
    a feed scrubber/stripper system
    a main wash column;
    a rectifier;
    an afterwash column;
    an acetylene fractionator;
    a butadiene fractionator;
    an acetylene washer;
    a solvent purification system; and
    a degasser and cooling column.

12. A process for recovering 1,3-butadiene from a $C_4$ fraction, comprising:
    feeding a hydrocarbon fraction containing butanes, butenes, 1,2-butadiene, 1,3-butadiene, $C_4$ acetylenes, $C_3$ acetylenes, and $C_{5+}$ hydrocarbons to a vaporization system;
    recovering a vapor fraction from the vaporization system;
    recovering a liquid fraction from the vaporization system;
    feeding the recovered vapor fraction to a butadiene extraction unit;
    recovering from the butadiene extraction unit a 1,3-butadiene fraction, a $C_3$ acetylene fraction, a $C_4$ acetylene fraction, one or more fractions comprising the butanes and butenes, and a fraction comprising the 1,2-butadiene and the $C_{5+}$ hydrocarbons;
    selectively hydrogenating at least one of the $C_3$ acetylene fraction and the $C_4$ acetylene fraction to produce a hydrogenated effluent comprising olefins, dienes, and oligomer byproducts;
    feeding the hydrogenated effluent and the fraction comprising the 1,2-butadiene and the $C_{5+}$ hydrocarbons to a separator to recover a heavies fraction comprising the $C_{5+}$ hydrocarbons and the oligomer byproducts and a lights fraction comprising the olefins, dienes, and 1,2-butadiene;

feeding the recovered liquid fraction to the separator as a reflux; and feeding the lights fraction to the butadiene extraction unit.

13. The process of claim 12, wherein the $C_4$ acetylene fraction comprises $C_4$ acetylenes and 1,2-butadiene.

14. The process of claim 13, wherein an amount of 1,2-butadiene in the $C_4$ acetylene fraction is approximately equal to an amount of the 1,2-butadiene in the feed hydrocarbon fraction.

15. The process of claim 13, wherein an amount of 1,2-butadiene consumed via the selectively hydrogenating is approximately equal to an amount of the 1,2-butadiene in the feed hydrocarbon fraction.

16. The process of claim 12, wherein vinylcyclohene is produced in the butadiene extraction unit or is present in the feed hydrocarbon fraction, the process further comprising:

recovering a fraction comprising the vinylcyclohexene from the butadiene extraction unit; and feeding the vinylcyclohexene fraction to the separator, wherein the vinylcyclohexene is recovered from the separator in the heavies fraction.

* * * * *